(12) United States Patent
Lanza et al.

(10) Patent No.: US 8,003,078 B2
(45) Date of Patent: Aug. 23, 2011

(54) TARGETED MR IMAGING AGENTS

(75) Inventors: Gregory M. Lanza, St. Louis, MO (US); Samuel A. Wickline, St. Louis, MO (US); Garry E. Kiefer, Richardson, TX (US); Phillip S. Athey, Lake Jackson, TX (US)

(73) Assignee: Barnes-Jewish Hospital, St. Louis, MO (US)

( * ) Notice: Subject to any disclaimer, the term of this patent is extended or adjusted under 35 U.S.C. 154(b) by 848 days.

(21) Appl. No.: 11/693,647

(22) Filed: Mar. 29, 2007

(65) Prior Publication Data
US 2007/0237721 A1 Oct. 11, 2007

Related U.S. Application Data

(60) Provisional application No. 60/786,873, filed on Mar. 29, 2006.

(51) Int. Cl.
*A61B 5/055* (2006.01)
(52) U.S. Cl. ............... 424/9.365; 424/1.65; 424/9.1; 424/9.3; 424/9.363; 424/9.361; 424/1.85; 424/1.89
(58) Field of Classification Search ............... 424/1.11, 424/1.49, 1.65, 1.69, 1.73, 1.81, 1.85, 1.89, 424/9.1, 9.2, 9.3, 9.32, 9.321, 9.322, 9.323, 424/9.34, 9.341, 9.35, 9.351, 9.36, 9.361, 424/9.362, 9.363, 9.364, 9.365, 9.37; 534/7, 534/10–16; 540/1, 450, 454, 455, 456, 457, 540/458, 459, 460, 461
See application file for complete search history.

(56) References Cited

U.S. PATENT DOCUMENTS

| | | | | |
|---|---|---|---|---|
| 5,707,605 A | * | 1/1998 | Meade et al. | 424/9.35 |
| 6,875,419 B2 | | 4/2005 | Sherry et al. | |
| 7,235,227 B2 | * | 6/2007 | Lanza et al. | 424/9.32 |
| 7,524,483 B2 | * | 4/2009 | Aime et al. | 424/9.365 |
| 2004/0030239 A1 | | 2/2004 | Van Zijl et al. | |
| 2005/0059881 A1 | | 3/2005 | Balaban et al. | |
| 2005/0191243 A1 | | 9/2005 | Aime et al. | |

FOREIGN PATENT DOCUMENTS

| | | |
|---|---|---|
| WO | WO-03/062198 | 7/2003 |
| WO | WO-2004/067483 | 8/2004 |

OTHER PUBLICATIONS

Woods et al., Chem. Soc. Reviews (2006) 35:500-511.
International Search Report and Written Opinion for PCT/US07/65533, mailed Jun. 13, 2008, 5 pages.
Winter et al., Magnetic Resonance in Medicine (2006) 56:1384-1388.

* cited by examiner

*Primary Examiner* — D. L. Jones
(74) *Attorney, Agent, or Firm* — Morrison & Foerster LLP

(57) ABSTRACT

MRI contrast agents that employ paramagnetic agents and chemical exchange saturation transfer (paraCEST) and which are coupled to targeted particulate delivery vehicles provide sufficient concentration of the paraCEST contrast agents to obtain useful images of target tissues or organs. In addition, the image contrast may be switched on or off with a presaturation radio frequency pulse, avoiding the necessity obtaining pre-injection and post-injection images.

14 Claims, 6 Drawing Sheets

TARGETED MR IMAGING AGENTS

CROSS-REFERENCE TO RELATED APPLICATIONS

This application claims benefit of provisional application U.S. Ser. No. 60/786,873 filed 29 Mar. 2006. The contents of this document are incorporated herein by reference.

STATEMENT OF RIGHTS TO INVENTIONS MADE UNDER FEDERALLY SPONSORED RESEARCH

This work was supported in part by grants from the National Institutes of Health and the Department of Defense. The U.S. government has certain rights in this invention.

TECHNICAL FIELD

The invention relates to magnetic resonance (MR) imaging agents that combine the features of paramagnetic contrast agents with contrast agents that employ chemical exchange saturation transfer (CEST) and are targeted to specific tissues or locations using particulate emulsions. In particular, the invention relates to derivatives of a tetraazacyclododecane-chelated lanthanide which comprises substituents containing slowly exchangeable NH or OH sites.

BACKGROUND ART

U.S. Pat. No. 6,875,419 ('419) to Sherry, et al., incorporated herein by reference, describes a class of paramagnetic metal ion based contrast agents which further employ chemical exchange saturation transfer (CEST). The contrast agents described in the '419 patent are derivatives of 1,4,7,10-tetraazacyclododecane-N,N',N'',N'''-tetraacetic acid (DOTA) wherein each of the four ring nitrogens is substituted by an acetamido containing substituent and contains a chelated metal ion. As described in this patent, images were obtained in solution independent of any targeted component. The images, however, are not sufficiently resolved or sufficiently bright to be useful in a physiological or diagnostic context. This is due to the relatively dilute concentration of the contrast agent.

The method relies on a combination of the paramagnetic relaxation effect of a chelated metal ion to shorten the bulk water relaxation time and the magnetization transfer effected by slowly exchangeable NH or OH in the side chains of a chelating agent after saturating the exchangeable proton using an appropriate radio frequency (RF); hence the term paraCEST. This has the advantage of allowing the image contrast to be switched on or off with a pre-saturation RF pulse, thus avoiding the necessity of obtaining pre-injection and post-injection images. A tutorial review explaining this technique is found in Woods, M., et al., *Chem. Soc. Reviews* (2006) 35:500-511.

The present applicants have found that a sufficient concentration of contrast agent may be obtained to permit the construction of a useful image if the contrast agent can be concentrated at a target.

It has thus now been found possible to utilize this technique to obtain images of, for example, blood clots by targeting the contrast agent to the location to be imaged. A similar approach with regard to paramagnetic based contrast agents has been described by the present applicants in PCT publication WO 2004/067483 published 12 Aug. 2004.

DISCLOSURE OF THE INVENTION

The invention is directed to "paraCEST" contrast agents that are coupled to targeted delivery vehicles for imaging of specific sites in vivo, and to methods to obtain MR images using these agents. The paraCEST agents decrease the magnitude of the bulk water signal, but permit direct comparison of signals with and without contrast agent in situ.

In one aspect, the invention is directed to a component of a targeted contrast agent which comprises a chelated lanthanide wherein the chelating moiety is substituted with one or more substituents comprising an OH or NH with an exchangeable proton, wherein the proton of the OH or NH is able to exchange with protons of bulk water at a rate faster than the relaxation time of bulk water under suitable MRI conditions, said chelate further linked to a spacer, which spacer terminates distal to the chelate in a moiety able to attach the contrast agent to a particulate delivery vehicle. The delivery vehicle is preferably a nanoparticulate or liposomal moiety wherein attachment can be effected by lipophilic interaction between the attachment moiety and the particulate or by covalent bonding. For use in imaging, the delivery vehicles will further contain a targeting ligand that is itself coupled to the delivery vehicles. Such coupling may be effected by means similar to those described above with respect to the extrinsic paramagnetic agents in WO 2004/067483. Optionally, the delivery vehicles may also contain therapeutic agents.

Typically, the chelating agent for the lanthanide is of the formulas (1)-(3)

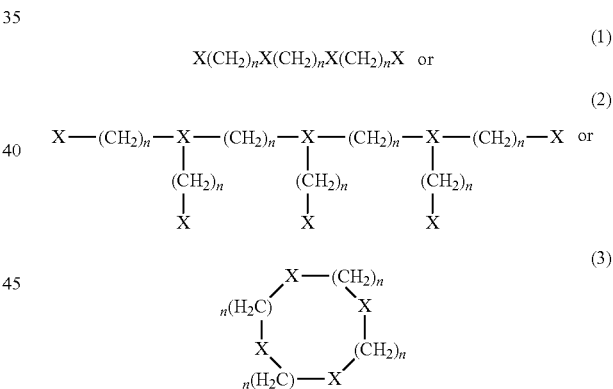

wherein each n is independently 1-3 and each X is independently O, OH, N, NH or $NH_2$ as mandated by the position of X in the chelating agent, and wherein at least one H is replaced by a moiety that contains a substituent that comprises an OH or NH having a proton exchange rate with bulk water faster than the relaxation time of bulk water under suitable MRI conditions. Further, in formulas (1)-(3), one H must be replaced by a spacer, coupled at the terminus distal to its point of attachment to the chelating agent, a lipophilic moiety or other agent for attachment to a particulate delivery vehicle.

In one embodiment, the invention is directed to compounds of the formula:

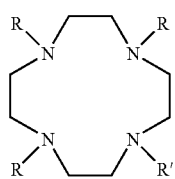

(4)

wherein at least one, and as many as four of said R groups is independently a substituent comprising an OH or NH having a proton exchange rate as described above, and wherein R' comprises a spacer coupled at the terminus distal to the tetrazole ring system, a lipophilic moiety or other agent for attachment to a particulate delivery vehicle.

In still another embodiment, the invention is directed to compounds of formula (5)

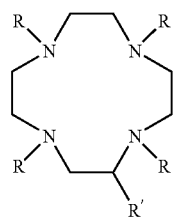

(5)

wherein at least one R is a substituent as defined above in formula (4), and R' comprises a spacer with an attachment moiety as above described.

As noted above, any of the chelating agents of formulas (1)-(5) may further include a lanthanide ion suitable for paraCEST imaging.

All of the foregoing chelating agents, under certain circumstances, will be present as their pharmaceutically acceptable salts. Where appropriate, the pharmaceutically acceptable salts of the chelating agents of the invention are included within its scope.

In other aspects, the invention is directed to emulsions of delivery vehicles coupled with any of the compounds of formula (1)-(5), and to methods of obtaining magnetic resonance images using these emulsions.

These imaging methods are able to allow the image contrast to be switched on and off. By administering a presaturation radio frequency (RF) pulse, associated with the exchangeable proton on the chelating agent, the signal can be effectively switched off. A subsequent interrogation without presaturation provides the desired image.

MODES OF CARRYING OUT THE INVENTION

Figure 1A:
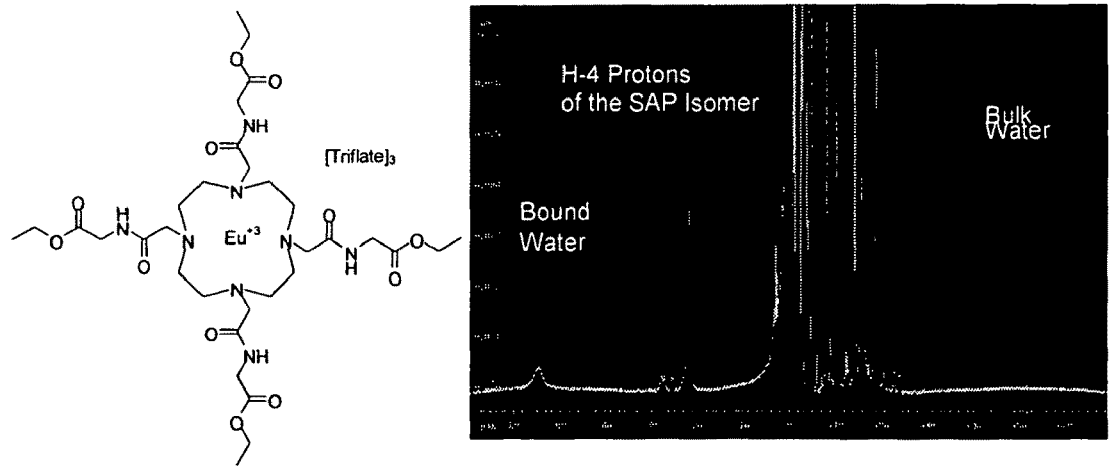
FIGS. 1A and 1B show a comparison of the NMR spectrum obtained from a prior art compound of Sherry (U.S. Pat. No. 6,875,419) with that of a derivatized form thereof.

Magnetic resonance imaging (MRI) is arguably the most powerful and important imaging modality in clinical medicine. It is non-invasive and can provide anatomical details about static structures and dynamic processes from any region of the human body. Conventional low-molecular weight, extracellular, largely Gd3+-based contrast agents have had a significant impact in diagnostic medicine. These agents enter all extracellular space (vascular plus interstitial) and highlight only those tissue regions that temporally accumulate the paramagnetic complex, because they affect the signal generated from the bulk water protons only in their proximity. This accumulation of paramagnetic complex results in a shortening of the bulk water spin-lattice relaxation time (T1) and hence brightening of the image in that region. This mechanism of altering bulk water relaxation cannot be controlled externally and hence one cannot modulate (turn on/off) the relaxation effects of a T1 shortening agent; one can only compare image intensities pre- and post injection of the agent.

In addition, one is dependent entirely upon getting enough agent targeted to a site of interest. Various estimates of the lower detection limit of a typical low molecular weight Gd3+-based complex with a relaxivity of ~4 mM−1s−1 have been made and these vary somewhat but are typically in the range of 100-500 M. There has been considerable effort put forth to engineer Gd3+-based complexes with substantially higher relaxivities which would permit lower concentrations, but only modest success has been achieved. Experts in this field agree that the only way to gain a substantial increase in relaxivity is to slow rotation of Gd3+ complexes by attachment to a larger structure such as biopolymer, a nanoparticle, or a naturally occurring polymer like albumin. Thus, to create new Gd3+-based systems for molecular imaging applications, a high molecular weight polymer must be used. This can introduce new complications and limitations that are not present with freely diffusible, low molecular weight complexes.

However, if the signal of the bulk water protons could be modulated with the contrast agent present, known signal modulation algorithms could be used to obtain a substantial gain in sensitivity even while using a low molecular weight complex.

In the paraCEST approach used in this invention, the contrast agent has at least one exchangeable proton that exchanges (physically) with the protons in bulk water. The chemical shift of that proton has to be offset from the chemical shift of bulk water—the more displaced the better. The exchange rate must be faster than the relaxation time of bulk water, so Gd can't be used because it speeds up the bulk water relaxation time too much. Eu can be used because it speeds up the relaxation time of bulk water enough to see a signal from bulk water, but it is slow enough to allow for the exchange.

To obtain an image that can be considered enhanced by the contrast agent, two readings are taken in situ.

The signal from the bulk water protons is read after exciting the exchangeable proton to saturation by applying an RF resonant with the exchangeable proton. (Signal A) When that is done, the bulk water signal (now read at the RF resonant with bulk water) is weaker because the exchangeable protons are diluting the protons in the water that can absorb the RF (at the water resonance) because they are already in an excited state.

The signal from the bulk water is also read using an RF appropriate for bulk water, but without presaturation of the exchangeable protons. (Signal B) The resulting signal B is stronger than signal A because the exchanged protons can still be excited by the RF.

Signal B minus Signal A provides the desired image.

The invention employs targeted particulate delivery vehicles to direct paraCEST contrast agents to a desired site in vivo. The site may be a blood clot, a tumor, an organ characterized by a surface moiety that binds to a particular ligand, or any other specific site displaying a binding partner for a targeting moiety coupled to the delivery vehicle. For example, activated proliferating endothelial cells are characterized by the integrin $\alpha_v\beta_3$ and a multiplicity of targeting agents for this integrin is known. See, for example, WO 2003/062198. In addition, blood clots characterized by fibrin can be targeted using antifibrin antibodies or fragments thereof.

By regulating the parameters of the resonance pulses, the image generated by the protons at the target site may be turned on and off. Saturation of the exchangeable proton in the contract agent at the resonance frequency essentially turns the signal generated by the bulk water protons off, and obtaining an image without such saturation turns the signal on so that signals with and without contract agent can be compared.

In addition, certain characteristics at the target can be measured by virtue of the effect of these conditions on the exchange rate of the relevant protons. See, for example, U.S. Pat. No. 6,875,419 in paragraph 4, incorporated herein by reference. While a change in these characteristics can be detected, the level of such physiological change, for example that of pH, lactate, glucose, and temperature, is generally not measurable due to the effect of concentration of contrast agent on the observed signal. In one embodiment of the invention, correction can be made for contrast agent concentration by measuring the concentration of fluoride containing delivery vehicles within a voxel using the magnetic resonance signal from fluorine nuclei. The signal generated by $^{19}F$ is also affected by the nature of its chemical environment, so by using a variety of delivery vehicles containing a variety of fluorocarbons, the concentration of various types of nanoparticles can be differentiated. Thus, measurements may be made simultaneously with respect to a number of targets in the same or separate locations or several different parameters can be measured.

The nature of the lanthanide included also affects the proton exchange rate and the distance from the chelated ion to which the effect on the exchange rate extends. Thus, substituting dysprosium for europium permits influence on the exchange rate of protons contained in the lipid/surfactant layer of nanoparticles in some embodiments of the invention or of liposomes in other embodiments.

In addition, the presence of lipids in delivery vehicles in some embodiments of the invention can be manipulated to offset toxicity of the paraCEST agent. For example, cationic paraCEST agents, which are often toxic, can be neutralized by anionic lipids in liposomes or in coated nanoparticles.

In one embodiment, the particulate delivery vehicles are characterized by lipophilic surfaces which permit lipophilic interaction with the attachment moieties of the derivatized paraCEST contrast agents of the invention. Such attachment moieties include phospholipids, sphingolipids, or di- or mono-glycerides which offer functional groups that permit coupling to a spacer. The lipid portions associated with these attachment moieties are then embedded in the lipid component of the delivery vehicles. Alternatively, the attachment moiety may comprise a functional group for use in covalent linkage to a component at the surface of the particulate delivery vehicle, independent of the nature of the particulate vehicle per se.

Delivery vehicles may include lipid carriers, liposomes, lipid micelles, lipoprotein micelles, lipid-stabilized emulsions, fluorocarbon nanoparticles, and polymer-lipid hybrid systems. Liposomes can be prepared as described in *Liposomes: Rational Design* (A. S. Janoff ed., Marcel Dekker, Inc., N.Y.), or by additional techniques known to those knowledgeable in the art. Liposomes used as carriers may also contain therapeutic lipids, which include ether lipids, phosphatidic acid, phosphonates, ceramide and ceramide analogues, sphingosine and sphingosine analogues and serine-containing lipids. Liposomes may also be prepared with surface stabilizing hydrophilic polymer-lipid conjugates such as polyethylene glycol-DSPE, to enhance circulation longevity. The incorporation of negatively charged lipids such as phosphatidylglycerol (PG) and phosphatidylinositol (PI) may also be added to liposome formulations to increase the circulation longevity of the carrier. These lipids may be employed to replace hydrophilic polymer-lipid conjugates as surface stabilizing agents. Embodiments of this invention may make use of cholesterol-free liposomes containing PG or PI to prevent aggregation thereby increasing the blood residence time of the carrier.

Micelles are self-assembling particles composed of amphipathic lipids or polymeric components that are utilized for the delivery of sparingly soluble agents present in the hydrophobic core. Various means for the preparation of micellar delivery vehicles are available and may be carried out with ease by one skilled in the art. For instance, lipid micelles may be prepared as described in Perkins, et al., *Int. J. Pharm.* (2000) 200(1):27-39. Lipoprotein micelles can be prepared from natural or artificial lipoproteins including low and high-density lipoproteins and chylomicrons. Lipid-stabilized emulsions are micelles prepared such that they comprise an oil filled core stabilized by an emulsifying component such as a monolayer or bilayer of lipids. The core may comprise fatty acid esters such as triacylglycerol (corn oil). The monolayer or bilayer may comprise a hydrophilic polymer lipid conjugate such as DSPE-PEG. These delivery vehicles may be prepared by homogenization of the oil in the presence of the polymer lipid conjugate.

In one embodiment, the delivery vehicles comprise a nanoparticulate system containing a fluorocarbon as a core and an outer coating that is a lipid/surfactant mixture. This provides a vehicle for binding a multiplicity of copies of one or more desired components to the nanoparticle. The construction of the basic particles and the formation of emulsions containing them, regardless of the components bound to the outer surface is described in U.S. Pat. Nos. 5,690,907; 5,780,010; 5,989,520; 5,958,371 and 6,548,046 incorporated herein by reference.

Preferably the fluorocarbon is a liquid such that the boiling point is higher than of body temperature—i.e., >37° C. Thus, fluorochemical liquids which have boiling points above 37° C. are preferred, more preferably above 50° C., and most preferably above about 90° C. The "fluorochemical liquids" useful in the invention include straight and branched chain and cyclic perfluorocarbons including perfluorinated compounds which have other functional groups. Perfluorinated compounds are preferred. Particularly preferred are compounds which will remain in the liquid state when they serve their function in the subject, i.e., in the case of the present invention, when used to obtain an MR image.

Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully perfluorinated including perfluoroalkylated ether, polyether or crown ether.

The coating which comprises lipid/surfactant to form an outer coating on the nanoparticles which will contain the coupled contains of the invention or entrap reagents for binding desired components to the surface include natural or synthetic phospholipids, fatty acids, cholesterols, lysolipids, sphingomyelins, and the like, including lipid conjugated polyethylene glycol. Various commercial anionic, cationic, and nonionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids included in the outer layer may be advantageous in entrapping ligands such as nucleic acids, in particular aptamers. Typical cationic lipids may include DOTMA, N-[1-(2,3-dioleoyloxy)propyl]-N,N,N-trimethylammonium chloride; DOTAP, 1,2-dioleoyloxy-3-(trimethylammonio)propane; DOTB, 1,2-dioleoyl-3-(4'-trimethyl-ammonio)butanoyl-sn-glycerol, 1,2-diacyl-3-trimethylammonium-propane; 1,2-diacyl-3-dimethylammonium-propane; 1,2-diacyl-sn-glycerol-3-ethyl phosphocholine; and 3β-[N',N'-dimethylaminoethane)-carbamol]cholesterol-HCl.

The lipid/surfactant coated nanoparticles are typically formed by microfluidizing a mixture of the fluorocarbon lipid which forms the core and the lipid/surfactant mixture which forms the outer layer in suspension in aqueous medium to form an emulsion. Sonication or other techniques may be required to obtain a suspension of the lipid/surfactant in the aqueous medium.

For coupling by covalently binding the targeting ligand and the compound of the invention to the components of the outer layer, various types of bonds and linking agents may be employed. Typical methods for forming such coupling include formation of amides with the use of carbodiimides, or formation of sulfide linkages through the use of unsaturated components such as maleimide. Other coupling agents include, for example, glutaraldehyde, propanedial or butanedial, 2-iminothiolane hydrochloride, bifunctional N-hydroxysuccinimide esters such as disuccinimidyl suberate, disuccinimidyl tartrate, bis[2-(succinimidooxycarbonyloxy)ethyl]sulfone, heterobifunctional reagents such as N-(5-azido-2-nitrobenzoyloxy)succinimide, succinimidyl 4-(N-maleimidomethyl)cyclohexane-1-carboxylate, and succinimidyl 4-(p-maleimidophenyl)butyrate, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. As noted above, the attachment moiety may be included in the surfactant layer if its properties are suitable, i.e., it contains a highly lipophilic portion, this will be embedded in the lipid/surfactant coating. Further, if the ligand is capable of direct adsorption to the coating, this too will effect its coupling. For example, nucleic acids, because of their negative charge, adsorb directly to cationic surfactants.

The particulate delivery vehicles of the invention, in addition to the paraCEST agents, include a targeting component or ligand. Typically, the targeting component or ligand is coupled to the particulate delivery vehicle by direct binding.

By "direct binding" of the ligand to the nanoparticle is meant that the ligand specific for a component characteristic of the targeted site is associated with the nanoparticle itself, as opposed to indirect binding effected through biotin/avidin. In the biotin/avidin mediated targeting methods of the art, the clot-specific ligand is coupled not to the emulsion, but rather coupled, in biotinylated form to the targeted tissue.

The targeting ligands cover a range of suitable moieties which bind to components of the target. In general, a component may itself be used to generate a ligand by using the component to raise antibodies or to select aptamers that are specific binding partners for the component. Alternatively, a suitable ligand may be known in the art. More generically, however, antibodies can be raised to desired components by conventional techniques and can be provided, preferably, as monoclonal antibodies or fragments thereof, or as single chain antibodies produced recombinantly. As the subject to be administered the compositions of the invention is human, it may be desirable to humanize antibody-type ligands using techniques generally known in the art. Further, suitable proteins or peptides which bind to targets can be discovered through phage-display techniques or through the preparation of peptide libraries using other appropriate methods. Selective aptamers which are able selectively to bind desired targets may also be prepared using known techniques such as SELEX™. (Aptamers are oligonucleotides which are selected from random pools for their ability to bind selected targets.)

In addition to the foregoing, peptidomimetics, which are small organic molecules intended to mimic peptides of known affinities can also be used as targeting agents.

In addition to the targeting ligands, the particulate delivery vehicles used in the compositions of the invention may contain ancillary agents, such as chemotherapeutic agents, pharmaceuticals, and the like. For example, the delivery vehicles may contain antiproliferative agents, anti-inflammatory agents, antimetabolites, and the like. Rapamycin, paclitaxel, and a variety of other pharmaceuticals may be included in the invention compositions.

As noted above, the chelating portions of the invention molecules are of formulas (1)-(5), wherein at least one substituent contains a proton exchangeable with bulk water and the chelating agent further comprises a spacer and an attachment moiety for embedding in the lipid portion of the delivery vehicles or other suitable attachment moiety.

In one embodiment, the substituents containing an exchangeable proton are of formula (6)

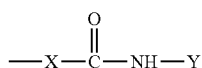

(6)

wherein X is optionally substituted alkylene (1-5C), preferably (1-3C) or an unsaturated form thereof and Y is optionally substituted alkyl (1-8C), preferably (1-3C) or an unsaturated form thereof. Optional substituents include, but are not limited to aryl, acyl, aroyl, heteroaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, =O, =NOH and/or $NO_2$, wherein each R is independently H, alkyl, alkenyl or aryl or the heteroatom-containing forms thereof, preferably the substituents are halo, SR, OR, $NR_2$, OCOR, NRCOR, $NRCONR_2$, $NRSO_2R$, $NRSO_2NR_2$, $OCONR_2$, CN, COOR, $CONR_2$, COR, and/or =O or more preferably halo, OR, $NR_2$ and/or =O.

The substituents must be such that the ability of H to exchange at the required rate is maintained. Thus, in one embodiment, the compounds of the invention have formula (7)

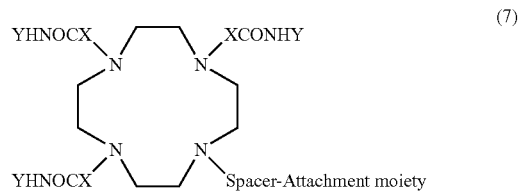

and in other embodiments, the invention compounds are of formula (8)

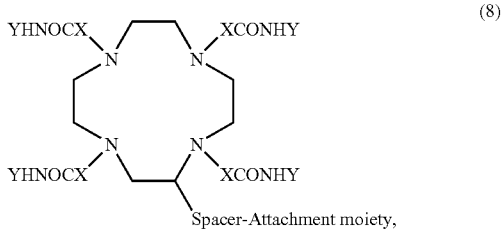

optionally comprising a lanthanide ion in each case.

Exemplary of the specific systems for use in the invention are shown below, wherein the lanthanide may be Pr, Nd, Eu, Dy, Tm or Yb.

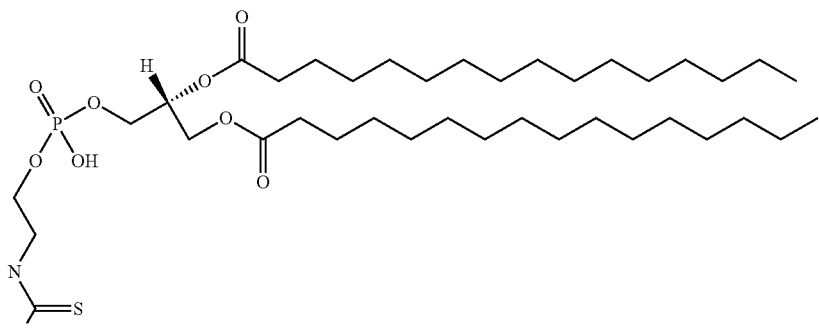

(9)

-continued
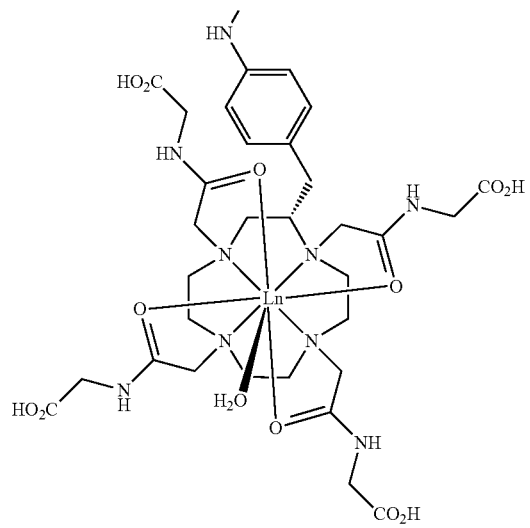
(10)
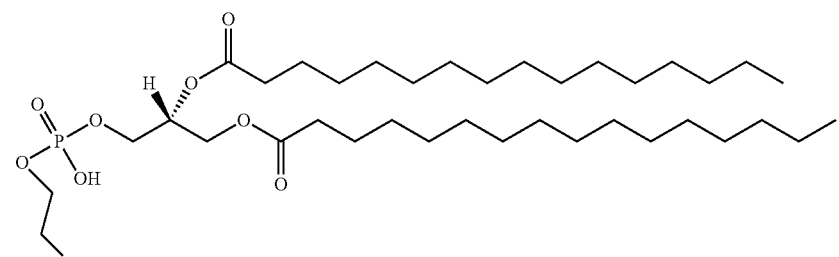
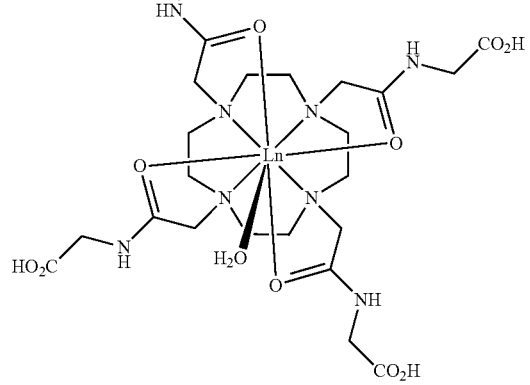
(11)
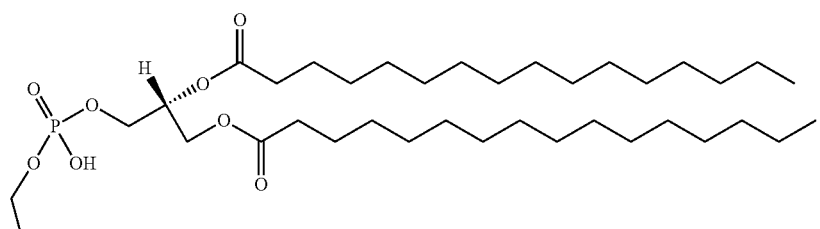

The synthesis of these compounds is shown below.
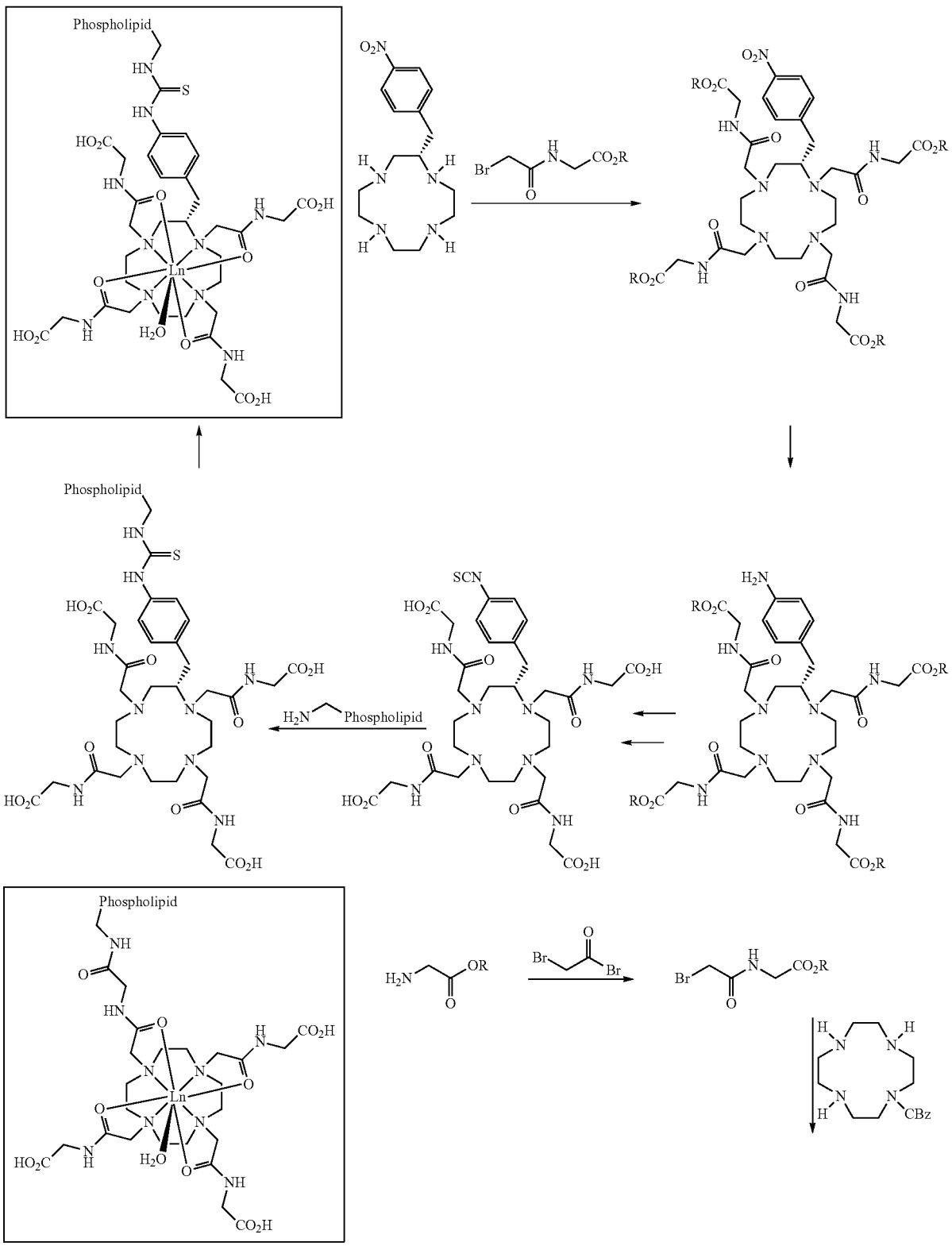

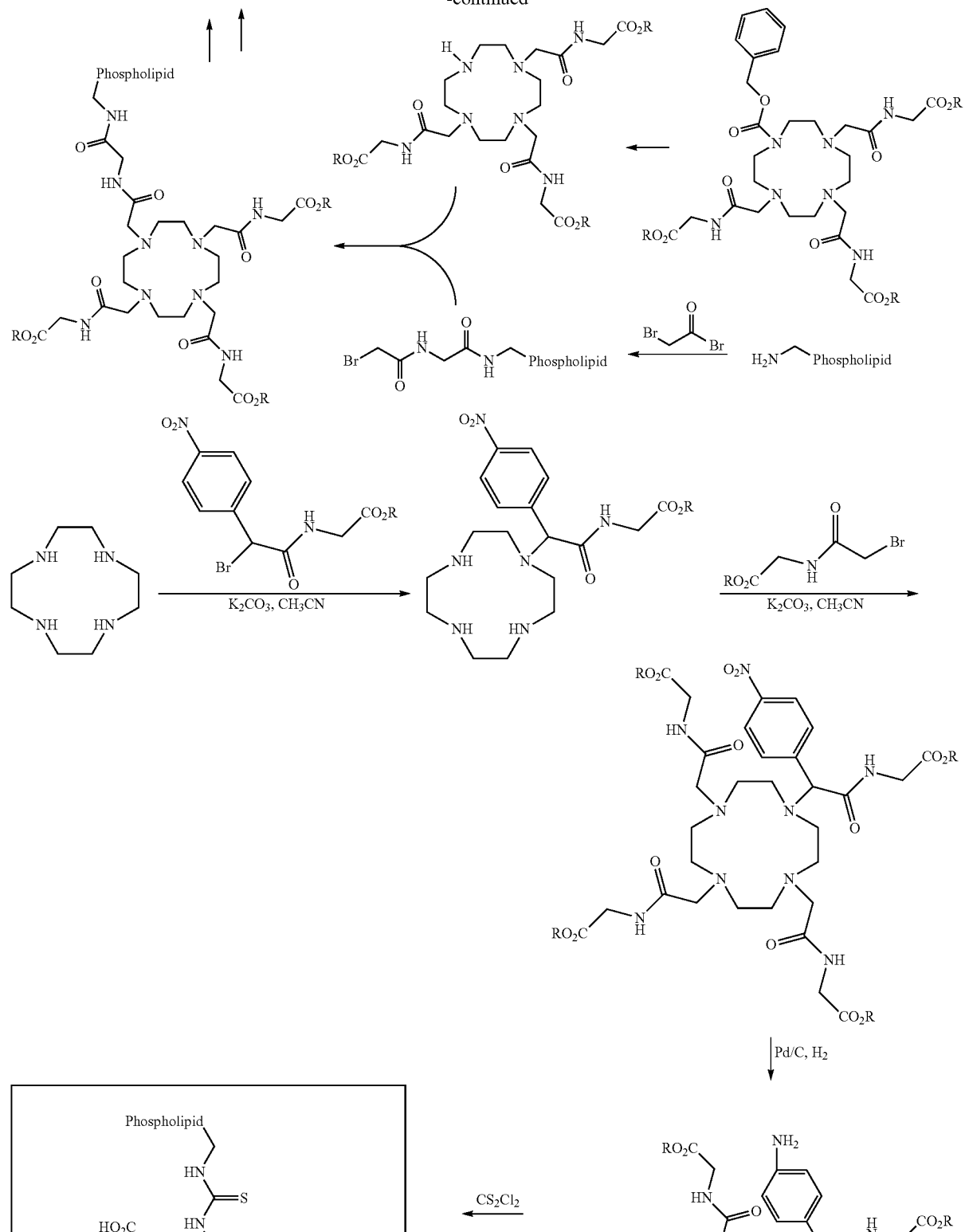
-continued

In one embodiment, invention compounds set forth above are conveniently associated with the lipid/surfactant layer of fluorocarbon nanoparticles, or the lipid surface of liposomes or other lipid-containing particulates. The nanoparticles will further comprise targeting ligands associated in a manner similar to that set forth, for example, in published PCT application PCT/US03/02380, which is incorporated herein by reference. In some embodiments, the particulate delivery vehicles further contain bioactive agents such as antiproliferative agents, hormones, anti-inflammatory agents, and the like.

For administration to a subject, typically the particulates are prepared as an emulsion.

Emulsions of the targeted particulates can be prepared in a range of methods depending on the nature of the components to be included in the coating. In a typical procedure, used for illustrative purposes only, the following procedure is set forth: Perfluorooctylbromide (40% w/v, PFOB, 3M), and a surfactant co-mixture (2.0%, w/v) and glycerin (1.7%, w/v) is prepared where the surfactant co-mixture includes 64 mole % lecithin (Pharmacia Inc), 35 mole % cholesterol (Sigma Chemical Co.) and 1 mole % dipalmitoyl-L-alpha-phosphatidyl-ethanolamine, Pierce Inc.) dissolved in chloroform. If therapeutic agents are to be included, a drug is suspended in methanol (~25 µg/20 µl) and added in titrated amounts between 0.01 and 5.0 mole % of the 2% surfactant layer, preferably between 0.2 and 2.0 mole %. The chloroform-lipid mixture is evaporated under reduced pressure, dried in a 50° C. vacuum oven overnight and dispersed into water by sonication. The suspension is transferred into a blender cup (Dynamics Corporation of America) with perfluorooctylbromide in distilled or deionized water and emulsified for 30 to 60 seconds. The emulsified mixture is transferred to a Microfluidics emulsifier (Microfluidics Co.) and continuously processed at 20,000 PSI for three minutes. The completed emulsion is vialed, blanketed with nitrogen and sealed with stopper crimp seal until use. A control emulsion can be prepared identically excluding the drug from the surfactant comixture. Particle sizes are determined in triplicate at 37° C. with a laser light scattering submicron particle size analyzer (Malvern Zetasizer 4, Malvern Instruments Ltd., Southborough, Mass.), which indicate tight and highly reproducible size distribution with average diameters less than 400 nm. Unincorporated drug can be removed by dialysis or ultrafiltration techniques. To provide the targeting ligand, an $F_{(ab)}$ fragment is coupled covalently to the phosphatidyl ethanolamine through a bifunctional linker in the procedure described above.

The following examples are intended to illustrate but not to limit the invention; in addition, appendix A describes an illustrative experiment.

Example 1

Preparation of Nanoparticles-1

Nanoparticles are prepared that comprise perfluorooctylbromide (40% w/v, PFOB), a surfactant co-mixture (2.0%, w/v) and glycerin (1.7%, w/v) and optionally an "oil" (2 to 10% w/v, substituted for the PFOB).

For various applications, the surfactant co-mixture includes therapeutic agents, dipalmitoylphosphatidyl choline, cholesterol, phosphoethanolamine-N-4 PEG (2000)-(p-maleimidophenyl)butyramide (MPB-PEG-PE) or phosphoethanolamine-(p-maleimidophenyl)butyramide, phosphatidylethanolamine, and sphingomyelin in varying molar ratios, which are dissolved in chloroform/methanol, evaporated under reduced pressure, dried in a 50° C. vacuum oven overnight and dispersed into water. For the paraCEST formulations of the invention, the surfactant co-mixture includes varying amounts of paraCEST chelates of formula (1) or (2) at overall concentrations of 2.5 to 50 mole %.

Oil (i.e., vegetable oil, vitamin E or other biocompatible "oil") may be added alone or may incorporate therapeutic agents. Lipophilic and hydrophobic therapeutic agents may be dissolved into the oil component up to supersaturating concentrations to increase total drug payload.

The above suspension is combined with PFOB and distilled, deionized water, blended and then emulsified at 10,000-20,000 PSI for three minutes.

Thiolated ligands are coupled to the maleimide derivatized phospholipid (or lipophilic substitute) in 50 mM phosphate, 10 mM EDTA buffer at pH 6.65 overnight under an non-oxidative atmosphere (i.e., nitrogen, argon). Small peptides and non-peptide molecules are coupled to the lipid moiety prior to emulsification.

Antibodies directed to targets are reacted with N-succinimidyl S-acetylthioacetate (SATA) for 30 min, dialyzed overnight, deprotected with hydroxylamine, dialyzed in oxygen free buffers, then coupled to the nanoparticles at room temperature. Alternatively, antibodies are enzymatically digested with papain or pepsin to yield $F_{(ab)}$ fragments isolated by routine affinity chromatography.

Particle sizes are determined in triplicate at ambient temperature with a laser light scattering submicron particle size analyzer (Malvern Zetasizer 4, Malvern Instruments Ltd, Southborough, Mass.), which typically indicates a highly reproducible size distribution with average diameters around 250 nm.

Example 2

Preparation of Nanoparticles-2

In this example, the chelating ligand of this invention and a targeting ligand are coupled to the nanoparticles prior to emulsification.

The nanoparticulate emulsions in this example are comprised of 20% (w/v) fluorochemical, 2% (w/v) of a surfactant co-mixture, 1.7% (w/v) glycerin and water representing the balance. The surfactant of control, i.e., non-targeted, nanoemulsions, includes 70 mole % lecithin (Avanti Polar Lipids, Inc.), 28 mole % cholesterol (Sigma Chemical Co.), 2 mole % dipalmitoyl-phosphatidylethanolamine (DPPE) (Avanti Polar Lipids, Inc.). Targeted nanoparticles are prepared with a surfactant co-mixture that includes: 70 mole % lecithin, 0.05 mole % N-[{w-[4-(p-maleimidophenyl)butanoyl]amino}poly(ethylene glycol)2000]1,2-distearoyl-sn-glycero-3-phosphoethanolamine (MPB-PEG-DSPE) covalently coupled to the targeting agent such as an antibody fragment or peptidomimetic, 28 mole % cholesterol, and 1.95 mole % DPPE. The components for each nanoparticle formulation are emulsified in a M110S Microfluidics emulsifier (Microfluidics) at 20,000 PSI for four minutes. The completed emulsions are placed in crimp-sealed vials and blanketed with nitrogen. Particle sizes are determined at 37° C. with a laser light scattering submicron particle size analyzer (Malvern Instruments).

Alternatively, the DSPE-PEG (2000) maleimide mercapto acetic acid adduct,

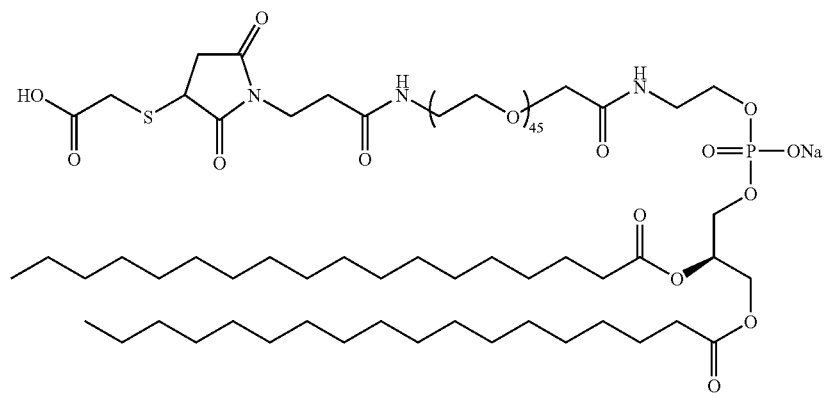

is prepared by dissolving 1,2-distearoyl-sn-glycero-3-phosphoethanolamine-N-[maleimide(polyethylene glycol) 2000] in DMF and degassing by sparging with nitrogen or argon. The oxygen-free solution is adjusted to pH 7-8 using DIEA, and treated with mercaptoacetic acid. Stirring is continued at ambient temperatures until analysis indicates complete consumption of starting materials. The solution is used directly in the reaction with a peptidomimetic or small peptide. The derivatized PEG-DSPE is combined at a 1:1 molar ratio with the mimetic or small peptide in 3 ml of $N_2$-purged, 6 mM EDTA. The round bottom flask is then mildly sonicated in a water bath for 30 minutes under a slow stream of $N_2$ at 37°-40° C. The mixture is swirled occasionally to resuspend all of the lipid film. This premix is added to the remaining surfactant components, PFC and water for emulsification.

For MR imaging, the paraCEST constructs of the invention are added in the emulsification step.

Example 3

Preparation of Nanoparticles-3

In this example, the ligands for imaging and targeting are coupled to the nanoparticles after emulsification.

The nanoparticulate emulsions in this example are comprised of 20% fluorocarbon, 2% (w/v) of a surfactant comixture, 1.7% (w/v) glycerin and water representing the balance. The surfactant of control, i.e., non-targeted, emulsions included 70 mole % lecithin (Avanti Polar Lipids, Inc.), 28 mole % cholesterol (Sigma Chemical Co.), 2 mole % dipalmitoyl-phosphatidylethanolamine (DPPE) (Avanti Polar Lipids, Inc.). Targeted nanoparticles are prepared with a surfactant co-mixture that includes: 70 mole % lecithin, 0.05 mole % N-[{w-[4-(p-maleimidophenyl) butanoyl] amino} poly(ethylene glycol)2000]1,2-distearoyl-sn-glycero-3-phosphoethanolamine (MPB-PEG-DSPE), 28 mole % cholesterol, and 1.95 mole % DPPE. The components for each nanoparticle formulation are emulsified in a M110S Microfluidics emulsifier (Microfluidics) at 20,000 PSI for four minutes. The completed emulsions are placed in crimp-sealed vials and blanketed with nitrogen until coupled. Particle sizes are determined at 37° C. with a laser light scattering submicron particle size analyzer (Malvern Instruments).

A free thiol containing ligand (e.g., antibody, small peptide, mimetic or antibody fragment) is dissolved in deoxygenated 50 mM sodium phosphate, 5 mM EDTA pH 6.65 buffer at a concentration of approx. 10 mg/ml. This solution is added, under nitrogen, to the nanoparticles in an equimolar ratio of the MPB-PEG$_{(2000)}$-DSPE contained in the surfactant to ligand. The vial is sealed under nitrogen (or other inert gas) and allowed to react at ambient temperature with gentle agitation for a period of 4 to 16 hours. Excess (i.e., unbound) ligand may be dialyzed against phosphate/EDTA buffer using a Spectra/Por "Dispodialyzer", 300,000 MWCO (Spectrum Laboratories, Rancho Dominguez, Calif.), if required.

Example 4

Comparison of NMR Spectra

Figure 1B:
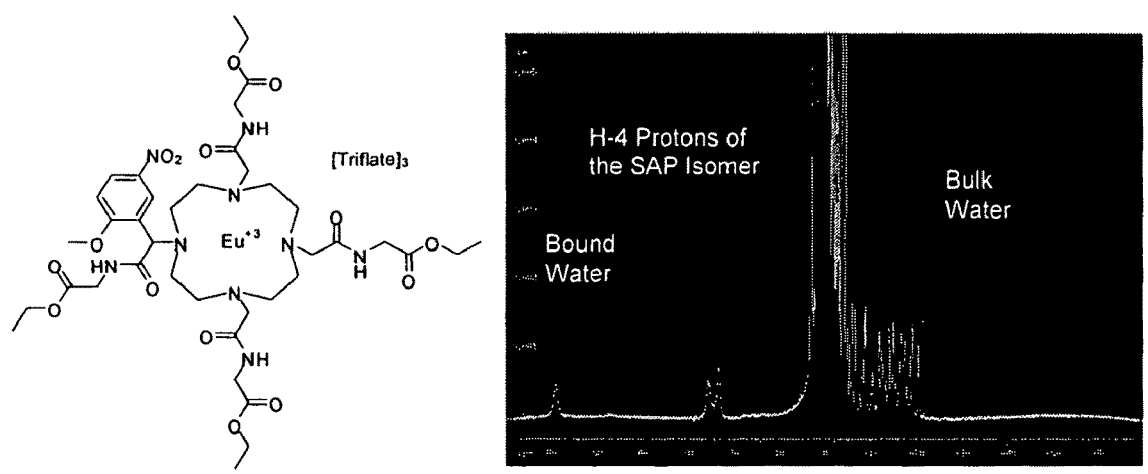

Initial spectroscopy work performed at 4.7 T using the prior art macrocycle (FIG. 1A) and the macrocycle modified for reaction to spacer (FIG. 1B) revealed nearly identical spectra.

Example 5

Blood Clot Imaging

ParaCEST nanoparticles consisted of 15% (v/v) perfluorooctylbromide (PFOB), 1% (w/v) surfactant comixture, 2.5% (w/v) glycerin and water for the balance. The surfactant comixture included 59 mole % lecithin, 1 mole % biotinylated dipalmitoylphosphatidylethanolamine, and 40 mole % of the paraCEST lipophilic chelate which is methoxy-DOTA bound to phosphatidylethanolamine through a capriole linker comprising chelated europium. The final europium concentration in the nanoparticle emulsion was 3.3 mM. All experiments were performed on a 4.7 T scanner at room temperature using a 2.5 cm circular surface coil. Bulk water spectra were collected from the neat nanoparticle emulsion with a 2 second pre-saturation RF pulse. The saturation frequency was varied from 100 to −100 ppm in 1 ppm increments to observe saturation transfer from the bound water. The integrated bulk water signals obtained by saturating at equivalent positive and negative frequency offsets were subtracted to produce a saturation profile for the paraCEST nanoparticles. Gradient echo images (TE=2.26 ms, TR=2.10 s, 312.5 by 312.5 μm in-plane resolution) were collected of a two-chamber phantom containing the neat nanoparticle emulsion in the inner chamber and deionized water in the outer chamber. The saturation pulses were applied at +52.5 ppm and −52.5 ppm and the images were subtracted to observe the paraCEST effect.

Figure 2:
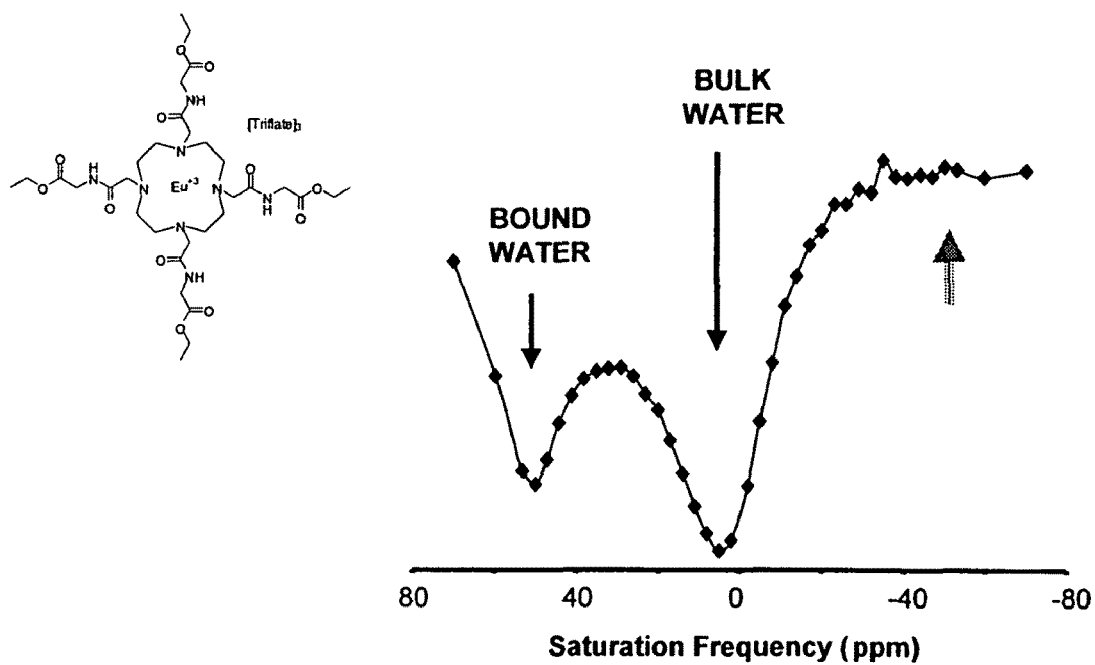
FIG. 2 shows the magnetization profile of the prior art compound as a function of saturation frequency.
Figure 3:
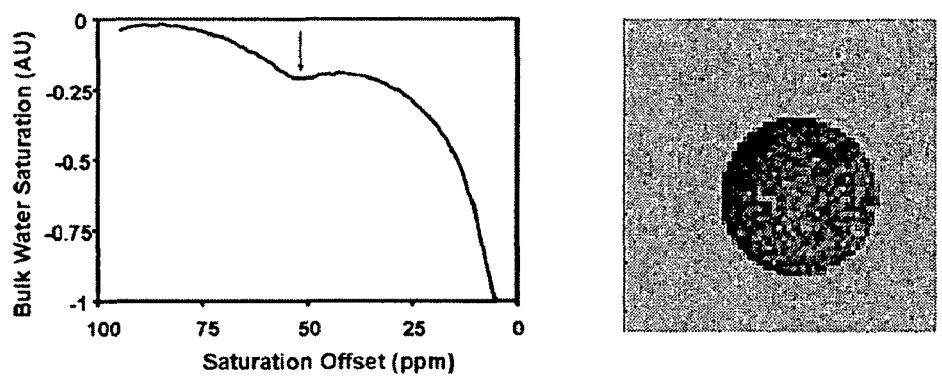
FIG. 3 shows the saturation of a bound water peak that transfers magnetization to the bulk water signal of the prior art agent.
Figure 4A:
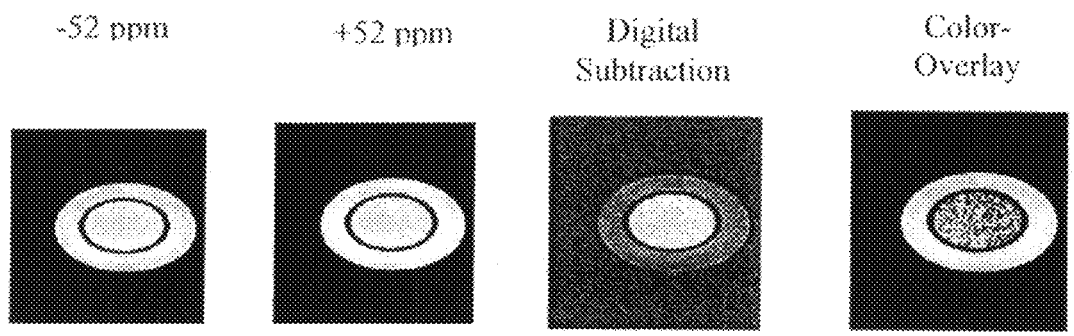
FIGS. 4A and 4B represent images obtained over a spectrum of RF manipulated by digital subtraction.
Figure 4B:
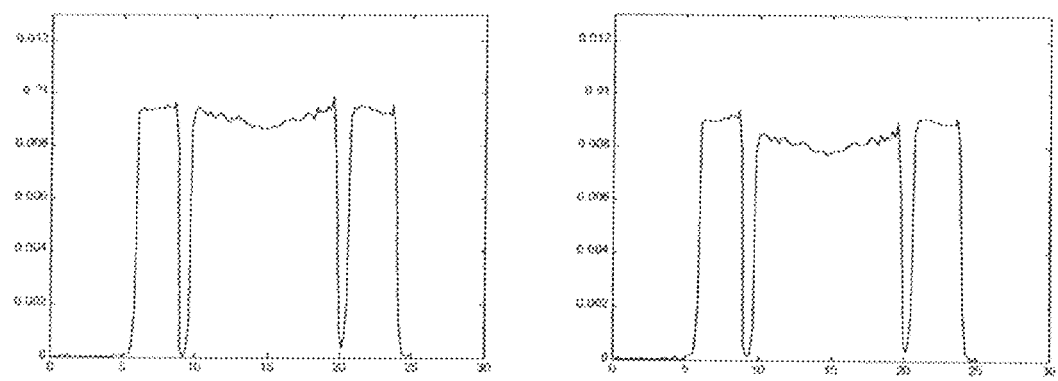

Nanoparticles formulated with paraCEST chelates displayed a marked saturation transfer effect at a saturation frequency of 52 ppm (FIG. 2). This represents saturation of the bound water peak at 52 ppm, which transfers magnetization into the bulk water signal, as shown for the parent europium-DOTA paraCEST agent. Phantom images clearly show a saturation transfer effect in the paraCEST chamber, but not in the chamber with normal water (FIG. 4). Cylindrical 5 mm-diameter clots were formed around a 5-0 silk suture suspended in sterile saline. Clots were serially incubated with 150 µg biotinylated antifibrin antibodies (1H10), 50 µg avidin, and 250 µl of paraCEST nanoparticles with rinsing between each step to remove unbound reactants. Clots were imaged using similar methods to those described above.

The attractiveness of CEST agents stems from the opportunity to activate contrast, effectively turning the contrast agent on and off at will by adjusting the pulse sequence parameters. This feature could allow robust detection of targeted contrast agents at a single time point without the need for subtracting images collected pre- and post-injection (1 to 2 hours apart) or the need to require align the images on a pixel by pixel basis to compensate for motion artifacts.

Figure 5:
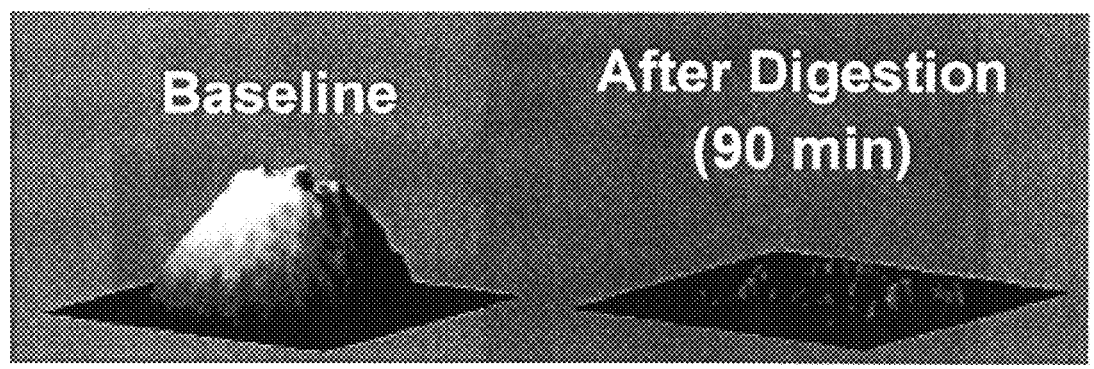
FIG. 5 shows an image of a clot before and after digestion using the contrast agents of the invention.

FIG. 5 shows a clot profile before and after digestion taken as described above.

Example 6

Preparation of ParaCEST Particles

Figure 6:
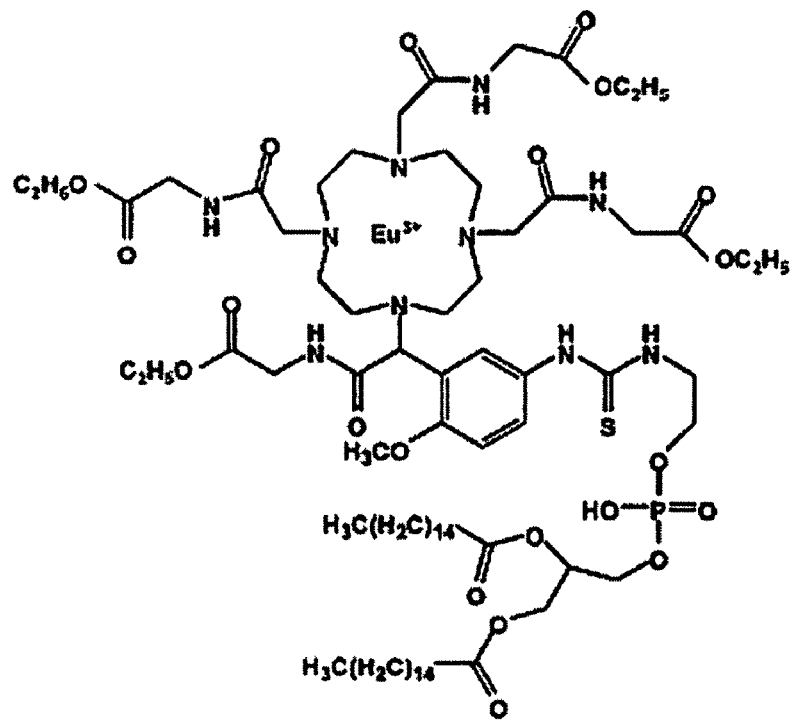
FIG. 6 shows the structure of a component employed in targeted paraCEST imaging as exemplified herein.

The para-CEST chelate used is shown in FIG. 6. Its synthesis is described. Kiefer et al. (2006), in press. A lipophilic tail, phosphatidylethanolamine (Avanti Polar Lipids, Inc.), was coupled to the compound through a thiourea linkage to form the final lipid conjugated compound, which was coupled with europium at equimolar concentrations to form the final paraCEST construct, $Eu^{3+}$-methoxy-benzyl-DOTA. Proton NMR spectroscopy was performed on the water soluble chelate (i.e., non-lipid conjugated) at 4.7 T revealing a distinct bound water peak at 52 ppm (data not shown), consistent with a previously reported symmetric paraCEST chelate.

Perfluorocarbon nanoparticles were prepared by emulsifying 15% (v/v) perfluorooctylbromide (PFOB; Minnesota Manufacturing and Mining), 1% (w/v) surfactant commixture, 2.5% (w/v) glycerin and water for the balance in a microfluidizer (Microfluidics, Inc.) for 4 minutes at 20,000 psi. paraCEST nanoparticle surfactant was comprised of phosphatidylcholine (Avanti Polar Lipids, Inc.), biotinylated dipalmitoylphosphatidylethanolamine (Avanti Polar Lipids, Inc.), and $Eu^{3+}$-methoxy-benzyl-DOTA at a molar ratio of 59:1:40, respectively. Control nanoparticles lacked the europium chelate, which was substituted with an equivalent increase in phosphatidylcholine.

Particle size, using quasi-elastic light scattering, and zeta potential, based upon an electrophoretic light scattering/laser Doppler velocimetry method, was measured in deionized water at 25° C. with a Brookhaven ZetaPlus analyzer (Brookhaven Instrument Corp.). The europium content of the emulsion was determined by standard comparator instrumental neutron activation analysis at the University of Missouri Research Reactor (MURR). Specifically, $Eu^{3+}$ was quantified by measuring the 842 keV gamma ray from the beta decay of $^{152m}Eu$ ($t_{1/2}$=9.31 h) produced through neutron capture by $^{151}Eu$. The samples and comparator standards were irradiated in a thermal flux of ~5×10$^{13}$ n/(s*cm$^2$) for 60 seconds, allowed to decay for several hours, and counted on a high-resolution gamma-ray spectrometer for 30 minutes. The minimum detection limit for this procedure is 2 ng of $Eu^{3+}$.

Incorporation of the $Eu^{3+}$-methoxy-benzyl-DOTA chelate into the nanoparticle surface produced an emulsion with similar physical characteristics as the control nanoparticles. paraCEST and control nanoparticles had similar diameters, 294 nm and 337 nm, respectively, which was moderately larger than previously reported due to a decrease in the percentage of surfactant lipids. The concentration of $Eu^{3+}$ in the paraCEST nanoparticle emulsion was 2.1 mM, whereas the control nanoparticles contained no detectable $Eu^{3+}$. The zeta potential of the control nanoparticles was −51.4 mV in deionized water, while the paraCEST nanoparticles were 53.8 mV, indicating that the $Eu^{3+}$ chelate carries a significant positive charge.

Example 7

Imaging Studies Using the Compositions Prepared in Example 6

Imaging and spectroscopy studies were performed on a 4.7 T Varian Inova scanner at room temperature (23° C.) using a 3 cm diameter custom-built circular surface coil. Bulk water spectra were collected from both paraCEST and control nanoparticle samples (50 µl) using a 2 second presaturation pulse at a power level of 28 dB. The saturation frequency was stepped between ±100 ppm (relative to the bulk water frequency at 0 ppm) in 1 ppm increments and the bulk water signal was integrated using a Matlab program (The Math Works, Inc.). The difference between the integrated signals measured at equivalent positive and negative saturation frequencies was plotted, yielding saturation transfer profiles for the paraCEST and control nanoparticles.

Figure 7:
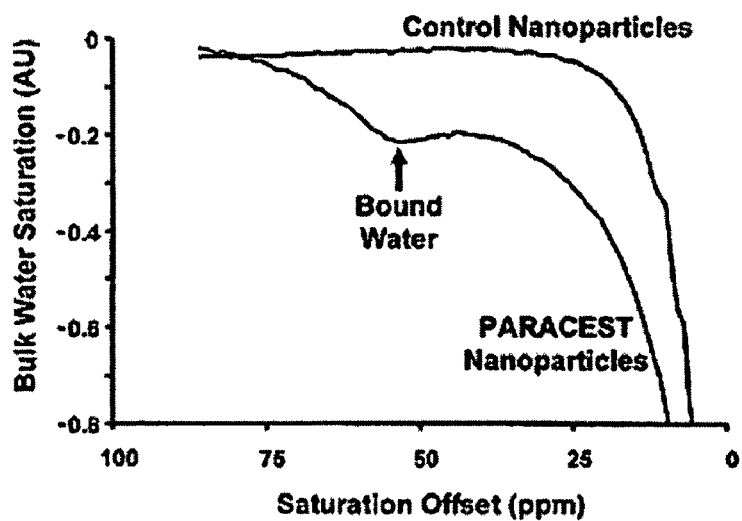
FIG. 7 is a graph showing the saturation of bulk water in contact with paraCEST nanoparticles as compared to control nanoparticles not containing paraCEST agents as a function of parts per million chemical shift.

ParaCEST nanoparticles displayed a marked saturation transfer effect at a presaturation frequency of 52 ppm (FIG. 7). This corresponds to saturation of the bound water peak at 52 ppm, which is transferred into the bulk water and decreases the signal acquired at 0 ppm. Control nanoparticles, however, did not show any appreciable saturation transfer at this frequency.

The effectiveness of the paraCEST nanoparticles was compared to control particles using a two-chamber phantom constructed with an inner 1 cm diameter chamber that contained the undiluted nanoparticle emulsion. The outer 1.8 cm diameter chamber contained phosphate buffered saline (PBS). Gradient echo images of the two-chamber phantom were collected using a 2.5 second presaturation pulse at a power level of 38 dB with a frequency offset of ±52 ppm relative to the bulk water peak. Other imaging parameters were: TR=2.52 s, TE=4.4 ms, number of averages=8, in-plane resolution=156 µm by 156 µm, slice thickness=4 mm. Image intensity was normalized with respect to the signal from the PBS chamber, images were subtracted pixel-by-pixel and saturation transfer signal enhancement was calculated. The signal enhancement of paraCEST nanoparticles was also measured following presaturation pulses of 1, 2 or 3 seconds duration at power levels of 26, 29, 32, 35 or 38 dB using low resolution imaging (TR=3.1 s, TE=2.9 ms, number of averages=2, in-plane resolution=390 µm by 390 µm, slice thickness=4 mm).

Figure 8:
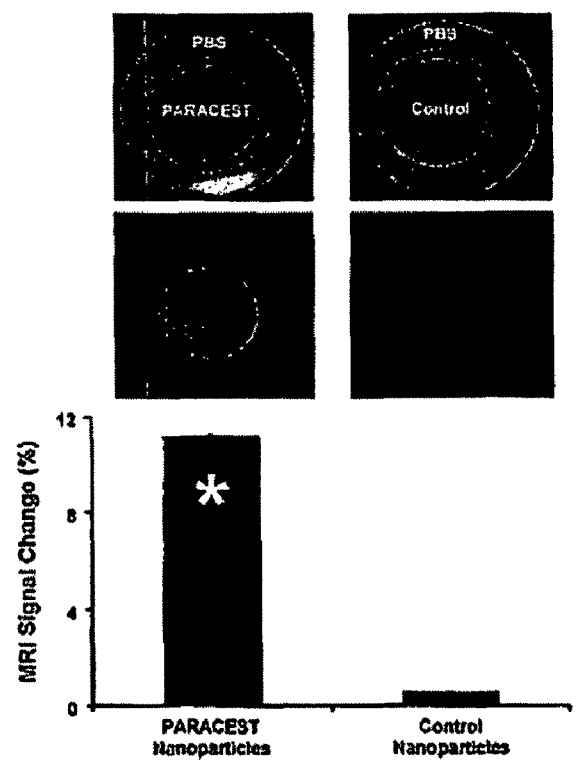
FIG. 8 shows images obtained with paraCEST particles as compared to control nanoparticles in a two-chamber system and a graph showing the contrast enhanced signal for paraCEST particles as compared to control nanoparticles.

Images of the two-chamber phantom collected with the saturation pulse at −52 ppm showed very similar signal intensity for paraCEST nanoparticles, control nanoparticles and PBS (FIG. 8). Subtracting the images collected with saturation at −52 ppm from the +52 ppm images revealed uniform paraCEST enhancement in the inner chamber, which was not observed with either control nanoparticles or PBS. paraCEST nanoparticles provided an image enhancement of 11.17±0.01% in comparison with the control nanoparticles, which provided very little contrast change (0.53±0.01%, *$p<0.05$).

Figure 9:
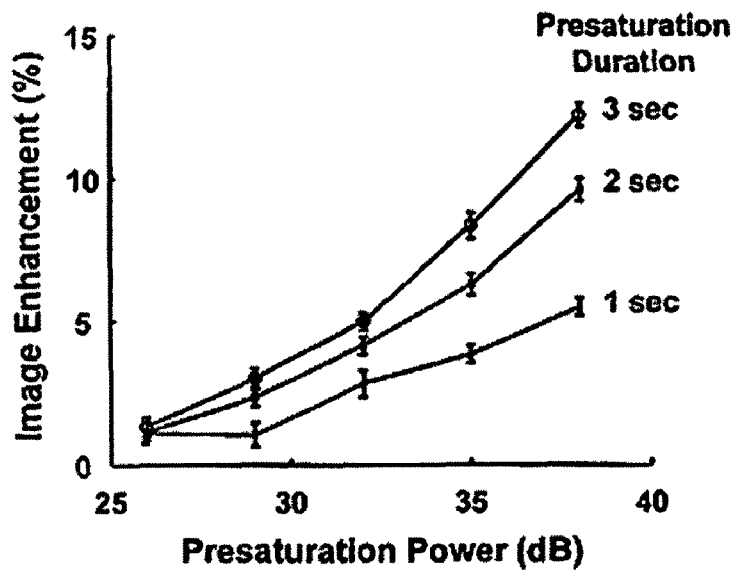
FIG. 9 is a graph showing image enhancement as a function of presaturation power and duration.

Increasing the duration and/or power of the presaturation pulse augmented the image enhancement obtained with paraCEST nanoparticles (FIG. 9). While the best results are obtained with a very long, high power presaturation pulse, it is evident that even a 1 second pulse with a power of 35 dB could produce adequate signal change to be reliably detected in an image. Since the paraCEST enhancement continued to increase, it is likely that the bound water peak was never completely saturated under any of our experimental conditions.

The concept of a fibrin-targeted paraCEST nanoparticle was studied using cylindrical plasma clots suspended in sterile saline inside plastic snap-cap tubes. The acellular clots were formed in a 5 mm diameter plastic mold prepared by combining fresh dog plasma, 100 mM calcium chloride (3:1 v/v), and 5 U thrombin around a 4-0 silk suture. Clots were serially incubated with 150 μg biotinylated anti-fibrin antibodies (1H10) overnight at 4° C., followed by 50 μg avidin for 1 hr at 25° C., and then 250 μl of paraCEST (n=5) or control (n=4) nanoparticles for 1 hr at 25° C. to complete the binding. Clots were rinsed three times with sterile saline after each incubation step to remove unbound reactants. Gradient echo images were collected of each clot using identical parameters as used for the two-chamber phantom. The clot surface was manually traced in Matlab and the contrast-to-noise ratio (CNR) was calculated relative to the standard deviation of the image intensity in air. The tracing was repeated in triplicate for each clot by a single observer and averaged.

Figure 10:
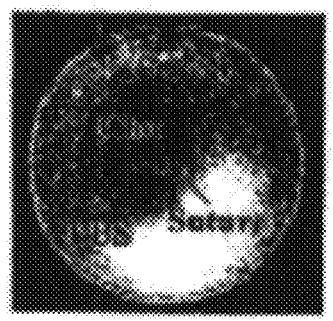
FIG. 10 shows images of clots obtained using paraCEST nanoparticles as compared to control nanoparticles and a graph showing contrast-to-noise ratios obtained with these compositions.
Figure 10:
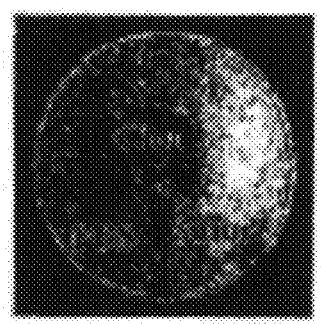
Figure 10:
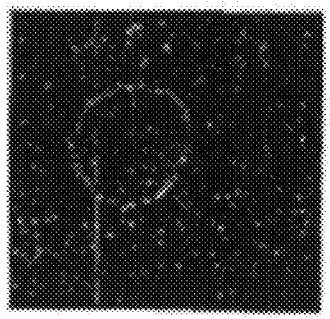
Figure 10:
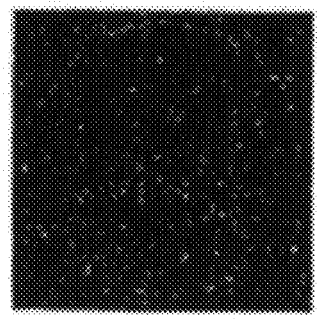
Figure 10:
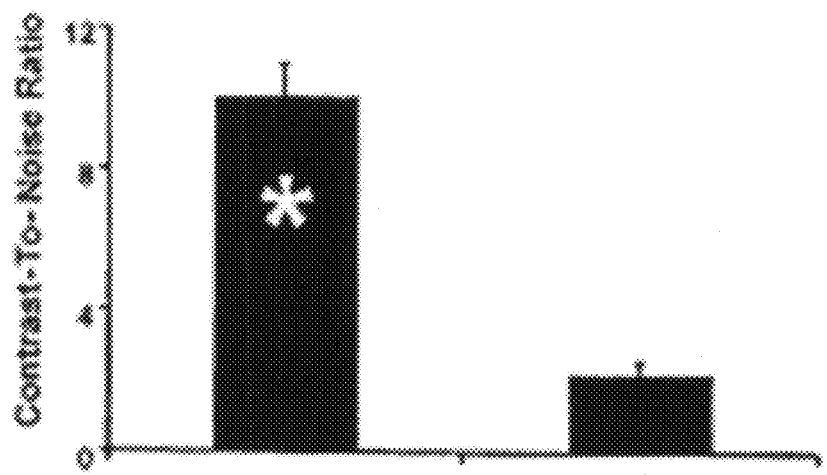

Clot images collected with presaturation at −52 ppm appeared very similar regardless of the nanoparticle treatment (FIG. 10). The clots displayed a uniform hypointensity with respect to the surrounding PBS, most likely as a result of magnetization transfer (MT) from proteins and macromolecules in the clot interacting with bulk water. These interactions widen the water peak resulting in some direct saturation of the bulk water peak even with the presaturation pulse offset by 52 ppm. Despite the MT effect, the surface of clots treated with fibrin-targeted paraCEST nanoparticles could be clearly distinguished after image subtraction. In contradistinction, the surface of clots treated with control nanoparticles could not be discriminated from noise upon subtraction. Averaged over the nine samples, CNR at the clot surface was significantly higher for fibrin-targeted paraCEST nanoparticles (10.0±1.0) compared to the control nanoparticles (2.2±0.4) (*p<0.05).

Statistical Analysis and Data Presentation

All studies followed a completely randomized design. Data were analyzed by student's t-Test or ANOVA. Means were separated when appropriate using the least significant difference (LSD) method and declared significant at an alpha level of 0.05 using a beta level of 0.80. Unless otherwise specified, averages are presented as a mean±SEM.

ParaCEST agents are often termed "negative" contrast agents, since saturation of the bound water peak of a paraCEST agent produces a decrease in the bulk water signal. However, the paraCEST contrast effect is displayed herein as signal enhancement, much like the effect of gadolinium, which is known as a "positive" $T_1$ contrast agent. In order to aid visualization, the −52 ppm image is subtracted from the +52 ppm image (activated image minus inactivated image) which converts the negative paraCEST effect into a positive signal. This technique produces subtraction images that show nanoparticle binding much more clearly and creates image "enhancement".

For application of paraCEST enhancement with targeted nanoparticles to biological systems, optimization of the chemistry, coil and pulse sequence is needed to optimize the results. The $Eu^{3+}$-methoxy-benzyl-DOTA chelate displayed a bound water peak both in solution as well as coupled to nanoparticles. However, 4.7 T may not be the optimal field strength, and the effects of lipid conjugation and particle incorporation on the water exchange kinetics can be manipulated. It may be desirable to assure more uniform saturation and sensitivity for in vivo imaging of deep tissues. RF deposition and imaging efficiency can also be optimized. Sequences utilizing multi-echo acquisitions or short saturation pulse trains may shorten imaging times and reduce RF deposition.

The invention claimed is:

1. A composition which comprises a chelating moiety, said chelating moiety linked to a spacer, which spacer is attached, distal to the chelating moiety, to a nanoparticle having a fluorocarbon core coated with a lipid surfactant, or a pharmaceutically acceptable salt of the chelating moiety; wherein said chelating moiety is of the formula:

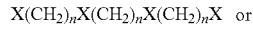

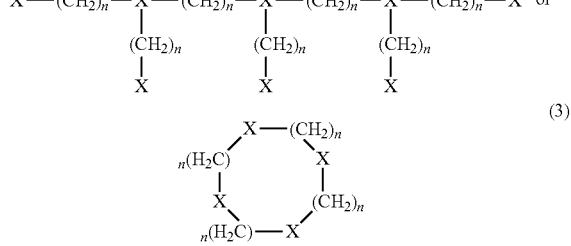

wherein each n is independently 1-3, and wherein each X is independently O, OH, N, NH or $NH_2$ as mandated by the position of X in said formulas, and wherein at least one H in said formula (1), (2) or (3) is replaced by a substituent of formula (6):

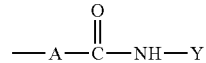

wherein A is an optionally substituted alkylene (1-5C) and Y is unsubstituted alkyl (1-8C) or $(CH_2)_m COOR''$ wherein m is 1-8 and R" is H, alkyl, alkenyl or aryl, and wherein one H in said formula (1), (2) or (3) is replaced by said spacer; and wherein said nanoparticle further comprises a targeting ligand.

2. The composition of claim 1, wherein said nanoparticle further comprises at least one therapeutic agent.

3. The composition of claim 1, which further comprises a chelated lanthanide ion.

4. The composition of claim 1, wherein the spacer comprises an amide linkage and/or polyethylene glycol.

5. The composition of claim 1, wherein the spacer comprises a phosphatidyl ethanolamine for attachment to said nanoparticle.

6. The composition of claim 1, wherein the chelating moiety and spacer is of the formula

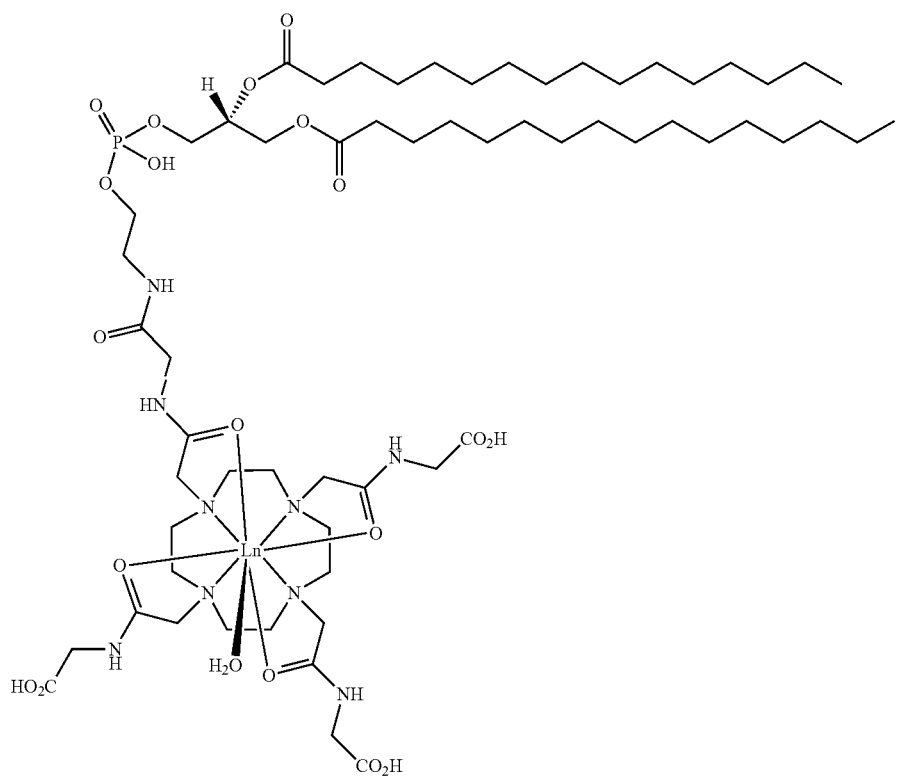
or of the formula
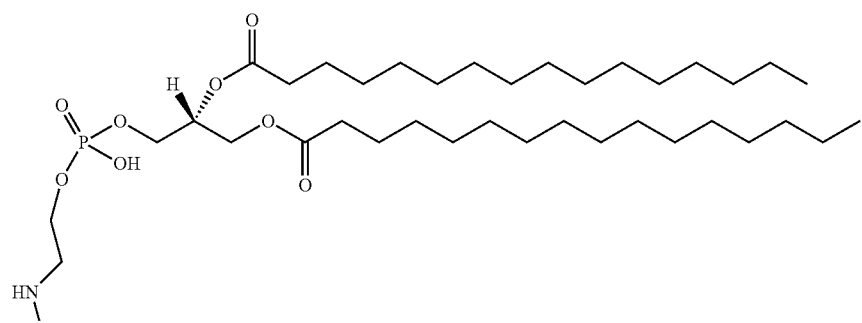

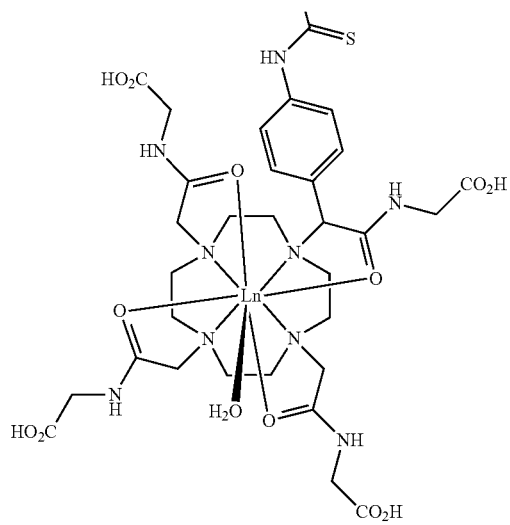
or is of the formula
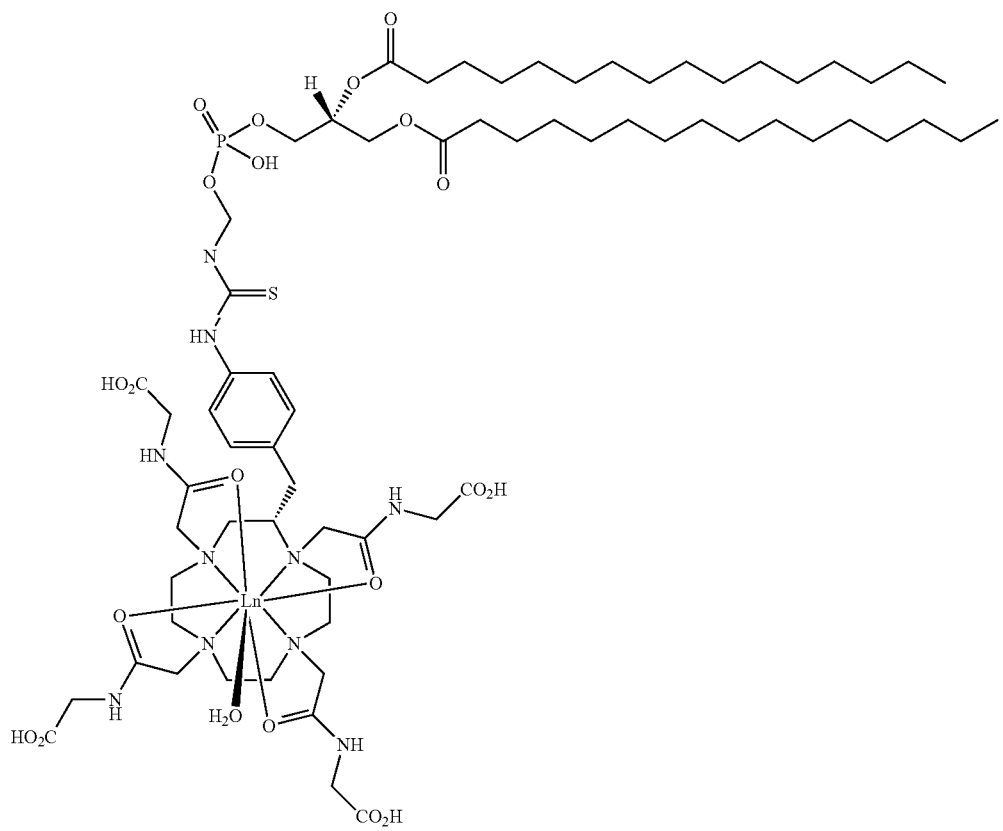
wherein Ln is optionally replaced by Pr, Nd, Eu, Dy, Tm or Yb;
or is of the formula (12)

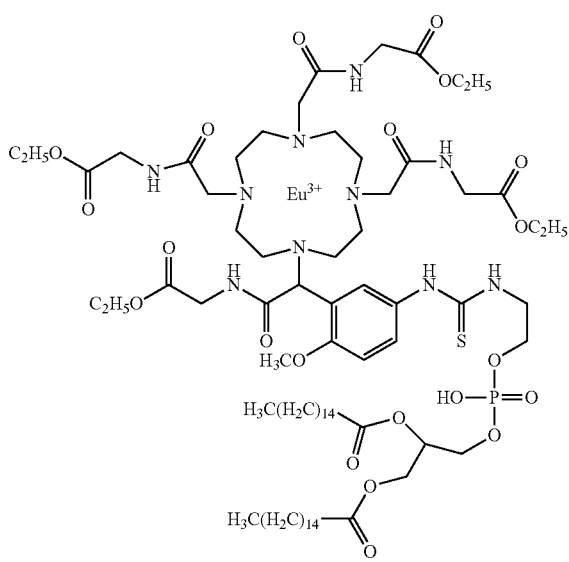

wherein Eu is optionally replaced by Ln, Pr, Nd, Dy, Tm or Yb.

7. A method to obtain a magnetic resonance image of a target tissue in a subject, which method comprises administering to said subject the composition of claim 1 wherein said chelator contains an Ln, Pr, Nd, Eu, Dy, Tm or Yb ion permitting the composition to reach said target tissue; and imaging said tissue.

8. The method of claim 7, wherein said image is obtained by saturating said composition with a radio frequency (RF) absorbed by an exchangeable proton in the substituent of formula (6) and subjecting the composition to an RF absorbed by bulk water to obtain a first image before or after subjecting the composition to an RF absorbed by bulk water without saturating with said RF to obtain a second image and subtracting the first image from the second image to obtain a contrast agent enhanced image.

9. A method to determine pH, lactate, glucose, or temperature at a target tissue in a subject, which method comprises
obtaining a contrast agent enhanced image at said target tissue according to claim 8 and obtaining a $^{19}F$ resonance image to determine the concentration of said composition.

10. The composition of claim 1 wherein said chelating moiety is of the formula:

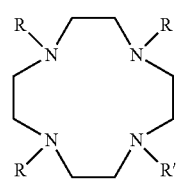

(4)

wherein at least one R group is a substituent of formula (6), and
wherein R' comprises said spacer, or
wherein the chelating moiety is of the formula

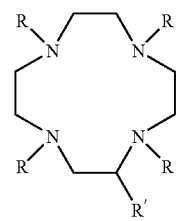

(5)

wherein at least one of said R groups is a substituent of formula (6) as defined in claim 1, and
wherein R' comprises said spacer, and
wherein said nanoparticle further comprises a targeting ligand.

11. The composition of claim 10, wherein said nanoparticle further comprises at least one therapeutic agent.

12. The composition of claim 10, which further comprises a chelated lanthanide ion.

13. The composition of claim 10, wherein the spacer comprises an amide linkage and/or polyethylene glycol.

14. The composition of claim 10, wherein the spacer comprises a phosphatidyl ethanolamine for attachment to said nanoparticle.

* * * * *